(12) United States Patent
Hartmann et al.

(10) Patent No.: US 8,057,444 B2
(45) Date of Patent: Nov. 15, 2011

(54) DEVICE FOR HOLDING A CANNULA AND FOR THE RELEASABLE ARRANGEMENT ON AN INJECTION PEN

(75) Inventors: Michael Hartmann, Melsungen (DE); Jürgen Fuchs, Bad Emstal (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 12/599,582

(22) PCT Filed: May 13, 2008

(86) PCT No.: PCT/DE2008/000799
§ 371 (c)(1),
(2), (4) Date: Jun. 17, 2010

(87) PCT Pub. No.: WO2008/138319
PCT Pub. Date: Nov. 20, 2008

(65) Prior Publication Data
US 2010/0262088 A1 Oct. 14, 2010

(30) Foreign Application Priority Data
May 10, 2007 (DE) .......................... 10 2007 022 404

(51) Int. Cl.
*A61M 5/00* (2006.01)
*B65D 83/10* (2006.01)

(52) U.S. Cl. ......... 604/263; 604/110; 604/264; 206/366

(58) Field of Classification Search .................. 206/366; 604/110, 240, 241, 263, 195, 198
See application file for complete search history.

(56) References Cited

U.S. PATENT DOCUMENTS

| 4,875,265 | A | | 10/1989 | Yoshida | |
|---|---|---|---|---|---|
| 5,092,462 | A | | 3/1992 | Sagstetter et al. | |
| 5,931,817 | A | * | 8/1999 | Nguyen et al. | 604/263 |
| 5,941,857 | A | * | 8/1999 | Nguyen et al. | 604/263 |
| 5,968,021 | A | | 10/1999 | Ejlersen | |
| 2005/0016883 | A1 | * | 1/2005 | Phan | 206/364 |
| 2010/0211014 | A1 | * | 8/2010 | Klint et al. | 604/173 |

FOREIGN PATENT DOCUMENTS

| EP | 0 441 628 A2 | 8/1991 |
|---|---|---|
| EP | 0 903 156 A2 | 3/1999 |
| EP | 0 903 157 A2 | 3/1999 |
| EP | 1 051 988 A2 | 11/2000 |
| EP | 1 396 234 A1 | 3/2004 |
| WO | WO 97/44078 | 11/1997 |

* cited by examiner

*Primary Examiner* — Kevin C Sirmons
*Assistant Examiner* — Bradley Thomas, Jr.
(74) *Attorney, Agent, or Firm* — RatnerPrestia

(57) ABSTRACT

A device for holding a cannula and for the releasable arrangement on an injection pen, with a basic body, wherein the cannula is arranged in the basic body in a manner such that it is substantially non-displaceable along the central axis thereof. Latching provisions are arranged on the circumferential surface of the basic body. The latching provisions are designed in order to be engaged behind by mating latching provisions of a release mechanism of a storage or disposal container for the device.

18 Claims, 6 Drawing Sheets

Section A-A

US 8,057,444 B2

DEVICE FOR HOLDING A CANNULA AND FOR THE RELEASABLE ARRANGEMENT ON AN INJECTION PEN

CROSS REFERENCE TO RELATED APPLICATIONS

This is a U.S. National Phase application of PCT application number PCT/DE2008/000799, filed May 13, 2008, which claims priority benefit of German application number DE 10 2007 022 404.6 (filed May 10, 2007), the content of such applications being incorporated herein by reference.

FIELD OF THE INVENTION

The invention relates to a device for holding a needle and for releasable arrangement on an injection pen.

BACKGROUND OF THE INVENTION

Such a device is disclosed in EP 1 396 234 B1, for example. The device there, designed as a pen needle and used to hold a needle, has webs which are distributed about the circumference of its hollow cylindrical main body and which extend from the proximal end in the direction of the distal end of the main body, and the webs open out into an elevation which is designed as a bead and which is formed at the distal end about the entire circumference of the main body. Depressions are formed about the circumference of the main body by the webs. These depressions begin at the proximal end of the main body and extend in the direction of the distal end thereof, but without reaching the distal end. The webs and depressions thus formed serve to release a used pen needle from an injection pen and at the same time to dispose of it in a suitable disposal container. When the pen needle is to be disposed of, it is fitted into an opening of the disposal container, which opening corresponds approximately to the dimension of the pen needle. Elements corresponding to the webs and depressions of the pen needle are arranged on this opening, about a part of the circumference, and form a negative image of the webs and depressions of the pen needle.

To release the pen needle, the injection pen is therefore inserted, with the pen needle toward the front, into the opening of the disposal container until the webs and depressions of the pen needle engage in the corresponding elements of the opening. In this position, the pen needle, which has been screwed with an inner thread onto an outer thread of the injection pen, is unscrewed from the injection pen and engaged from behind by an abutment. Thereafter, the injection pen is moved away from the opening of the disposal container. Ideally, the pen needle with its webs and depressions should then release itself from the corresponding elements of the opening and drop into the disposal container, in which it is then safely stored.

However, it has been shown that, with the pen needle thus released from the injection pen, the elevation extending about its entire circumference at the open end and designed in particular as a bead catches on or becomes wedged in the elements of the disposal container that correspond to the webs and depressions of the pen needle. The pen needle therefore sticks in the opening of the disposal container and is not yet safely disposed of therein. To complete the safe disposal in the container, it is necessary in such a case for the stuck or wedged pen needle to be pushed by hand or with a tool into the disposal container. In doing so, there is a risk that the person wishing to dispose of the pen needle may be injured by the needle protruding from the opening of the disposal container.

Such a needlestick injury is of course also associated with a not inconsiderable risk of life-threatening infection under some circumstances, since such devices for injection of liquids may be used by persons with highly infectious diseases.

In other pen needles according to the prior art, the pen needle is likewise engaged from behind by an abutment on the disposal container during release, in which case a gap is created between pen needle and injection pen, such that the known pen needles can be released from the injection pen by means of engagement from behind. To this extent, all of the known pen needles are dependent on the geometry of the injection pen from which they are released.

SUMMARY OF THE INVENTION

In light of the above, an object of the invention is to make available a device with which the safe disposal of the pen needle in a disposal container or the safe storage of the pen needle in a storage container is simplified, and with which the risk of infection and injury of the person disposing of the pen needle is greatly reduced. Moreover, the device is intended to be independent of the geometry of the injection pen from which it is released.

By virtue of the fact that latching means are arranged on the circumferential surface of the main body and are designed to be engaged from behind by mating latching means of a release mechanism of a storage or disposal container for the device according to aspects of the invention. Upon release of the device according to aspects of the invention from an injection pen and upon disposal in a disposal container or storage in a storage container, this measure effectively prevents the device from becoming wedged or caught on an opening of the disposal container or storage container. After the device according to aspects of the invention has in fact been fitted into the opening of the disposal or storage container, the connection or coupling between the device for injection of liquids and the device according to aspects of the invention is released and the injection pen is guided away from the opening. By virtue of the design according to aspects of the invention, the latching means of the device according to aspects of the invention engage in the mating latching means of the release mechanism of the disposal or storage container when inserted therein for release. After removal of the injection pen, the latching means of the device according to aspects of the invention release themselves from the mating latching means of the release mechanism of the disposal container, and the device then drops unimpeded into the latter. This is because neither the device itself nor the opening is provided with elements that could cause the device to become caught or wedged in the opening and could impede the drop into the disposal container. It has also proven advantageous if a certain play is present between the latching means of the device according to aspects of the invention and the mating latching means of the release mechanism of the disposal container during release, so as to prevent the device becoming clamped tightly within the opening. In the case of a storage container that is generally designed only to receive one device according to aspects of the invention, and that can also be in the form of a protective cap for a needle holder, the special geometry of the latching means and mating latching means ensures a secure hold of the device according to aspects of the invention in the storage container and prevents the device from sliding out again.

If a pen needle arranged on an injection pen is fitted in a septum of a liquid-filled cartridge arranged in the injection pen, the needle may remain in the septum when the pen needle is released, while the pen needle is otherwise already completely released from the injection pen, and unimpeded disposal of the pen needle would then not be guaranteed. To ensure that the pen needle is not pulled out again with the injection pen from the opening of the disposal container, the mating latching means of the release mechanism engage behind the latching means of the pen needle. Upon withdrawal of the injection pen, the pen needle is held securely by these undercuts of the latching means and of the mating latching means until the needle has been released completely from the septum. The pen needle can then drop unimpeded into the disposal container.

A further advantage of this invention is that diabetics in particular, who rely on regular injections of insulin with injection pens and who often have significantly impaired vision on account of their disease, obtain haptic and acoustic feedback from the latching means and mating latching means, when the device according to aspects of the invention is locked in the release mechanism of the disposal or storage container.

A further advantage over the prior art is that the special geometry of the device according to aspects of the invention ensures that the latching means and mating latching means already engage in one another before the pen needle has been released from the injection pen. In particular, the invention of the release mechanism is independent of the geometry of the injection pen.

According to a first advantageous embodiment, it has proven advantageous to design the latching means as simple webs. For such latching means designed as webs, the mating latching means can be provided in a simple way, for example as simple cuttings.

According to a further advantageous embodiment of the invention, the latching means have rear abutments that are designed to be engaged from behind by rear abutments of the release mechanism of a storage and disposal container for the device. This measure easily ensures a secure locking of the latching means and mating latching means, such that accidental release of the locked connection is ruled out.

It has also proven advantageous that the latching means also have lateral abutments that are designed to be engaged from behind by lateral abutments of the mating latching elements of the release mechanism of a storage or disposal container for the device. This ensures that the latching means and mating latching means do not come loose from each other as a result of inadvertent twisting of the device according to aspects of the invention within the release mechanism.

Particularly if the latching means of the device according to aspects of the invention are designed as webs, it is also advantageous to design the mating latching means as recesses in the release mechanism. This ensures secure fixing of the latching means and mating latching means to each other.

To ensure simpler and safer handling, the latching means are distributed uniformly about the circumference of the main body. Analogously, the mating latching means are distributed uniformly about the circumference of the release mechanism.

To prevent the latching means from becoming wedged in the release mechanism, and to thereby ensure safe release of the device according to aspects of the invention from the release mechanism, it has proven advantageous if the latching means extend substantially from the proximal end of the main body to substantially the center of the latter.

To further maximize this effect, the latching means are arranged substantially in the central area of the main body.

The main body of the device according to aspects of the invention is advantageously designed as a hollow cylinder, which can easily be connected to the injection pen.

For this purpose, the hollow cylindrical main body has coupling means that are designed to engage with mating coupling means of an injection pen in order to permit releasable arrangement thereon.

In a first embodiment, the coupling means is provided as an inner thread in the hollow cylindrical main body and is designed to engage with an outer thread of a needle seat of a device for injection of liquids.

Alternatively, it is of course possible for the coupling means to be in the form of at least one latching means which is provided in the hollow cylindrical main body and is designed to engage with at least one mating latching means of a needle seat of a device for injecting liquids. It is thus possible for the device to be easily fitted onto the mechanism for injection of liquids and released from the latter again, without it having to be provided with an inner thread and the mechanism having to be provided with an outer thread. Such latching and mating latching means ensure a secure fit and simple and rapid fastening and release of the device from the mechanism for injection of liquids.

It has proven advantageous to provide, as connecting means, at least one clip element which is designed to engage with at least one mating clip element on a needle seat of an injection pen. Such clip elements ensure safe and easily releasable coupling, which is technically simple and inexpensive to produce.

The invention further relates to a disposal or storage container for the above-described device according to aspects of the invention.

Further aims, advantages, features and possible uses of the present invention will become clear from the following description of the illustrative embodiments and by reference to the drawings. All of the features described here and/or shown in the drawings represent, either singly or in any desired advantageous combination, the subject matter of the present invention, and they do so independently of their presentation in the claims and of the back references indicated in the claims.

DETAILED DESCRIPTION OF EXEMPLARY EMBODIMENTS OF THE INVENTION

Figure 1:
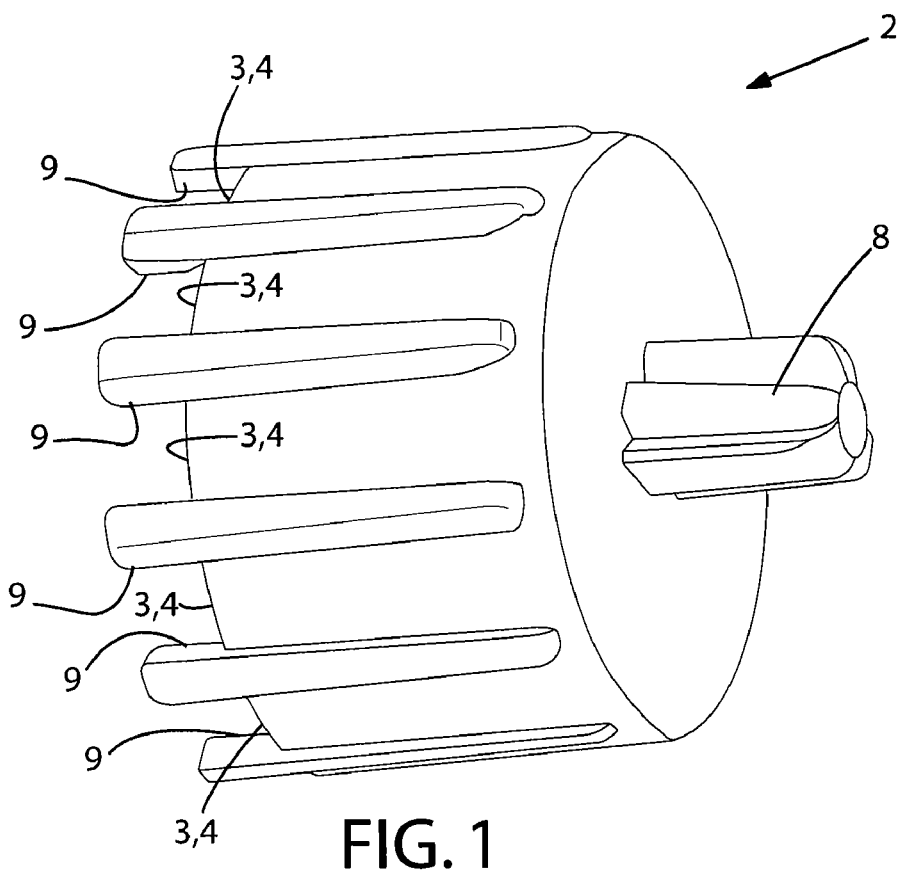
FIG. 1 shows a perspective plan view of the main body of an embodiment of the device according to aspects of the invention in the form of a pen needle.
Figure 2:
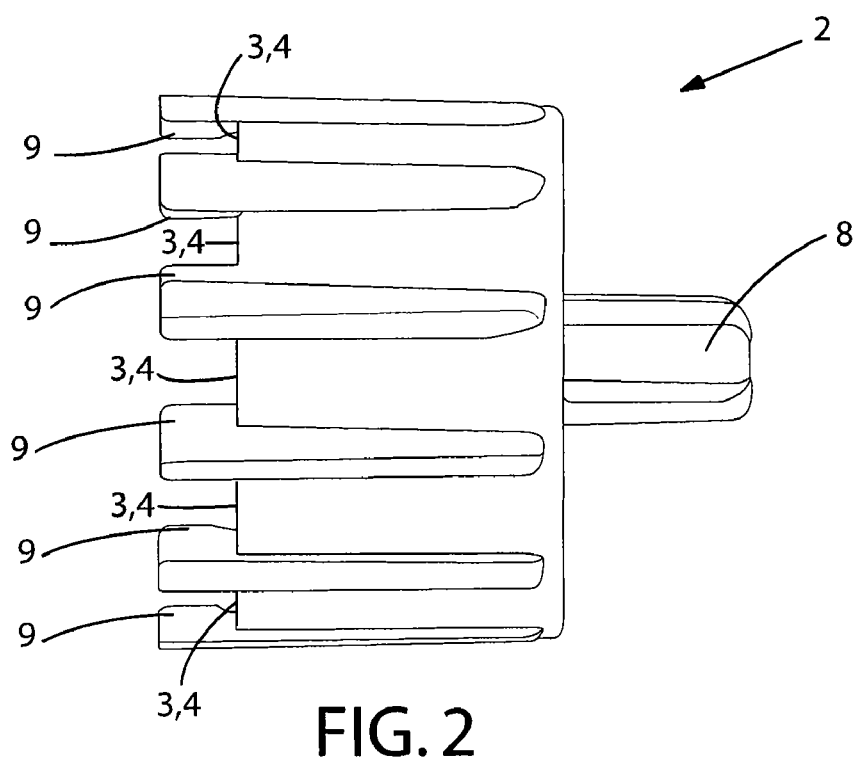
FIG. 2 shows the main body according to FIG. 1 in a side view.

The illustrative embodiment of a device according to aspects of the invention shown in FIGS. 1 to 4 is designed as a pen needle for an injection pen. The pen needle is composed principally of a main body 2 and of a needle (not shown), which is held secure against displacement therein. In the illustrative embodiment shown, the main body 2 is designed as a hollow cylinder with a closure element 19 at its proximal end, which closure element 19 forms the closure of the closed end of the main body 2. A reinforcing element 8 for the needle (not shown) is arranged centrally on the closure element 19 in such a way that the central longitudinal axis 8 of the main body coincides with the central longitudinal axis of the reinforcing element. As the name itself says, the reinforcing element 8 serves to reinforce the needle 1 in the area of the closure element and to ensure that forces acting on the needle are taken up and conveyed into the main body 2.

Latching means 3, or cuttings and elevations, are arranged on the circumferential surface of the hollow cylindrical main body 2. In the illustrative embodiment shown, the depressions and elevations extend as mutually parallel and straight webs from the closed proximal end to the open distal end of the main body 2. In the area of the open end of the main body 2, the elevations extend beyond the main body 2, or the depressions are designed as cuttings through the whole jacket thickness of the main body 2.

Figure 3:
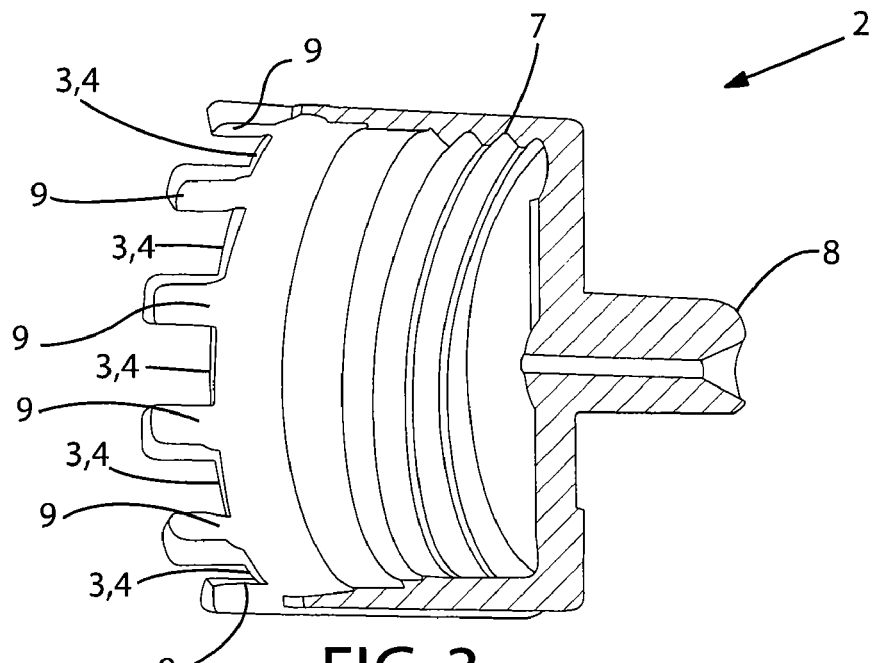
FIG. 3 shows the main body according to FIG. 1 in a perspective cross-sectional view.
Figure 4:
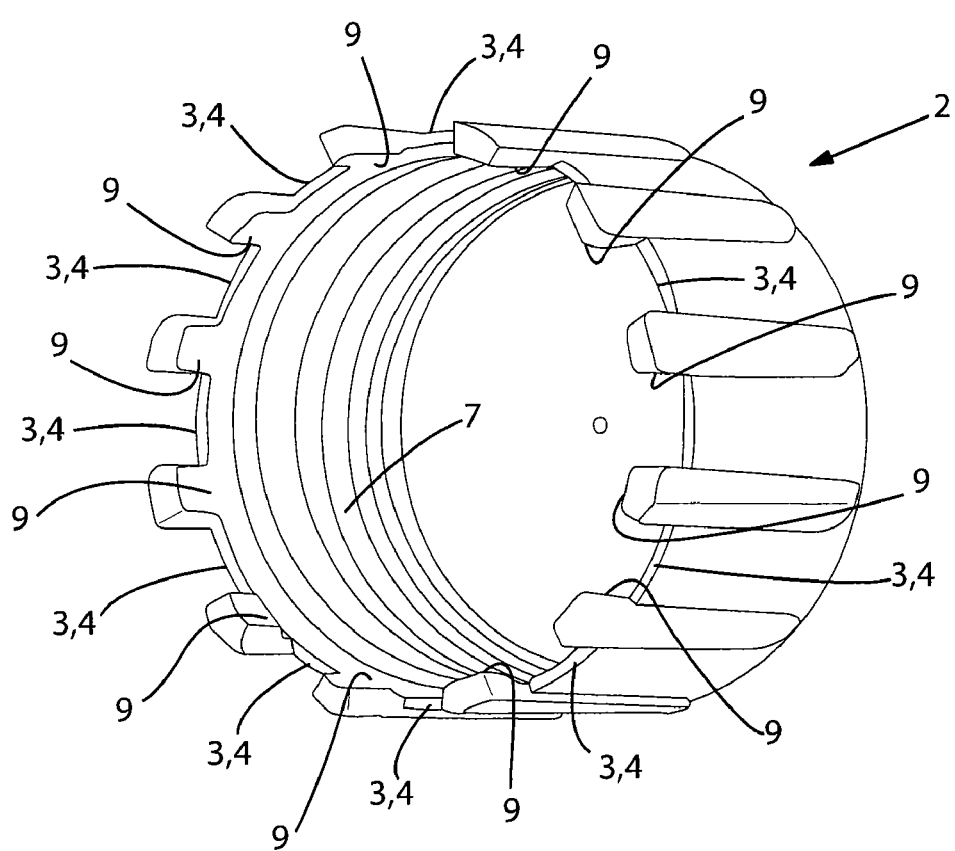
FIG. 4 shows the main body according to FIG. 1 in another perspective view.

As can be seen in particular from FIGS. 3 and 4, the hollow cylindrical main body 2 has, on its inside, an inner thread 7, which is adapted to an outer thread of an injection pen, such that a releasable connection between pen needle and injection pen can be established by means of the two threads. In addition, or even alternatively, the releasable connection between pen needle and injection pen can also be established by a connecting means 7a which is arranged on the pen needle and which engages with a connecting means (not shown here) arranged on the injection pen. In the present illustrative embodiment in FIGS. 1 to 4, the connecting means 7a is designed as an undercut 9 formed on the elevations and pointing toward the interior of the main body. The mating latching means are in this case in the form of a depression (not shown) on the injection pen or a clip element or spring element. A separate depression can be provided for each undercut. However, it is also possible, particularly if the undercuts all lie in one plane, to design a depression running round the surface of the injection pen as a mating latching means for the undercuts 9.

To arrange the pen needle on an injection pen, the corresponding outer and inner threads and, if appropriate, the further connecting means of the pen needle and of the injection pen are brought into engagement with one another, and the pen needle is thus fitted releasably on the injection pen. In this process, the needle (not shown) penetrates, with its end protruding into the hollow space of the main body 2 of the pen needle, through a septum of a medicament cartridge arranged in the injection pen. The medicament can then be administered with the aid of the injection pen. The medicament from the inside of the cartridge emerges through the needle of the pen needle.

To dispose of a used pen needle arranged on an injection pen, the injection pen, with the pen needle toward the front, is inserted into a release mechanism 21 designed as an opening in a disposal container 20. This opening is designed in such a way that some of the elevations and depressions of the cylindrical main body 2 of the pen needle engage in corresponding elements inside the opening, but with sufficient play being present to avoid the pen needle becoming stuck in the opening. When the elevations and depressions of the pen needle are in engagement with the corresponding elements of the opening, it is possible, by means of the two threads, and by turning the injection pen and releasing the connecting elements 7, 9 of the pen needle from the connecting elements of the injection pen, to release the pen needle from the latter. In doing this, abutments 24 of the mating latching means 23 of the release mechanism 21 engage behind rear abutments 4 of latching means 3 of the needle holder. When the injection pen is then guided away from the opening, the needle of the pen needle releases itself from the septum of the medicament cartridge, and the pen needle then drops unimpeded into the disposal container, since neither the pen needle nor the release mechanism 21 has elements that could lead to the pen needle becoming clamped, caught or wedged in the release mechanism 21.

A further illustrative embodiment is shown in FIGS. 5 to 9. The pen needle shown there, in the same way as in the illustrative embodiment according to FIGS. 1 to 4, can be connected with its main body 2 releasably to the injection pen 10 by means of outer and inner threads and/or connecting means. In this illustrative embodiment of the pen needle according to the invention, the needle 1 held in the central axis 4 of the main body 2 is shown.

In this illustrative embodiment, the pen needle is arranged on the injection pen analogously to the procedure described in relation to the illustrative embodiment in FIGS. 1 to 4.

However, the elements provided for releasing the pen needle from the injection pen and for safely disposing of the pen needle differ from the first-described illustrative embodiment. As can be seen in particular from FIG. 5, latching means 3 designed as webs are arranged on the hollow cylindrical main body 2 of the pen needle. The latching means 3 extend on the circumferential surface of the main body 2 substantially parallel to the central longitudinal axis 10 thereof and in the longitudinal direction thereof. They begin in the area of a closure element 3 arranged at the closed proximal end of the main body 2, and they end approximately at the center of the circumferential surface of the main body 2. In this illustrative embodiment too, the needle 1 is held in a reinforcing element 8, which can also serve to hold a protective cap for the needle 1.

Figure 5:
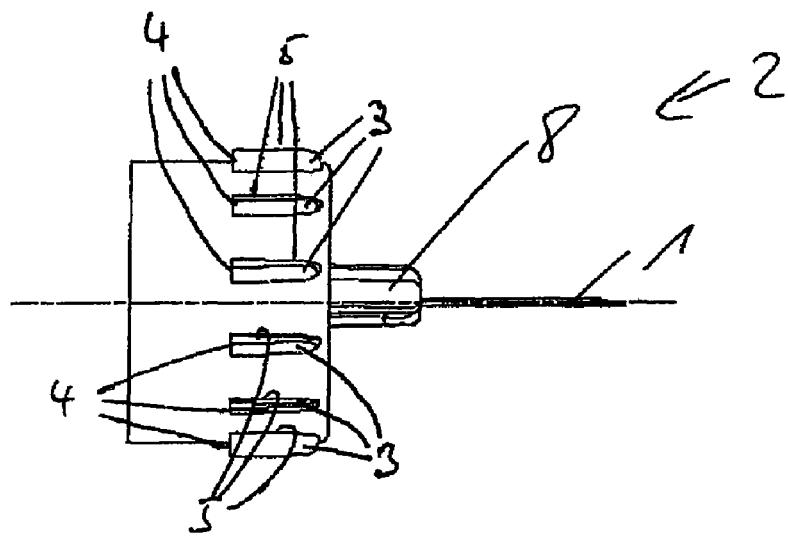
FIG. 5 shows a side view of another illustrative embodiment of the device according to aspects of the invention in the form of a pen needle.

FIGS. 6 to 9 of this illustrative embodiment show different views of the pen needle according to FIG. 5 arranged on an injection pen 11, which pen needle is already inserted, for release from the injection pen 11, into an opening of a release mechanism 21 of a disposal container 20.

Figure 6:
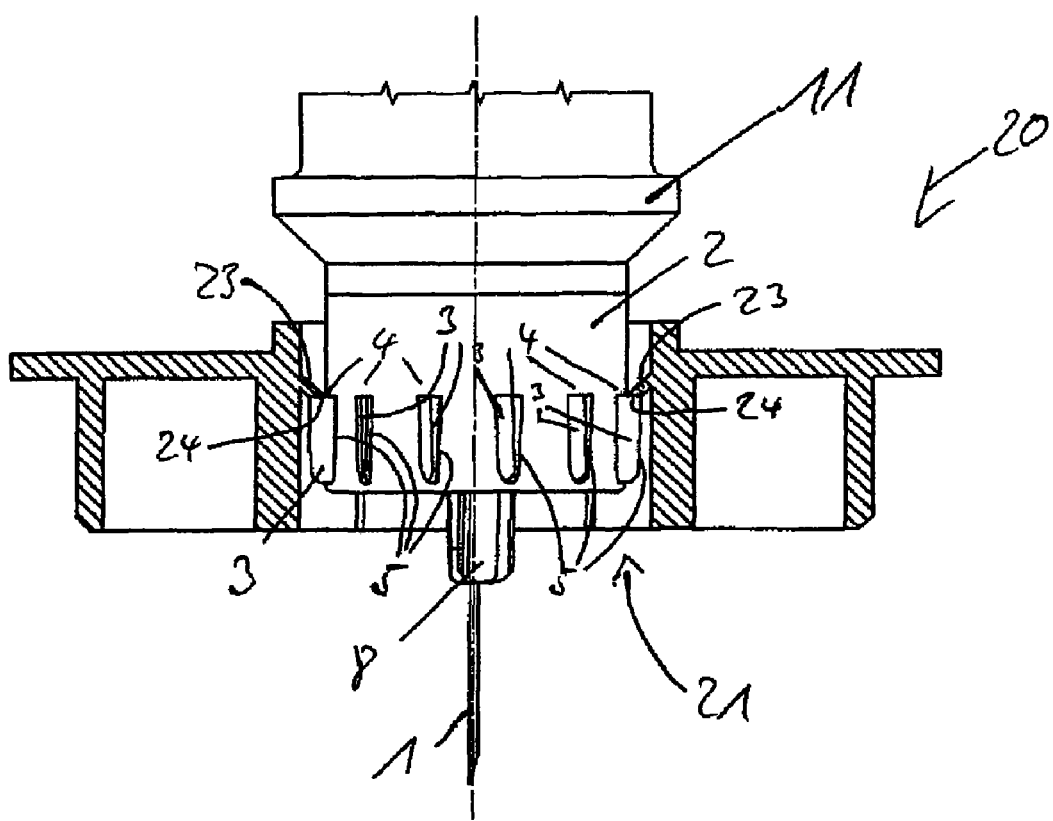
FIG. 6 shows an injection pen with a pen needle, according to FIG. 5, which is inserted for release in an opening of a disposal container.
Figure 8:
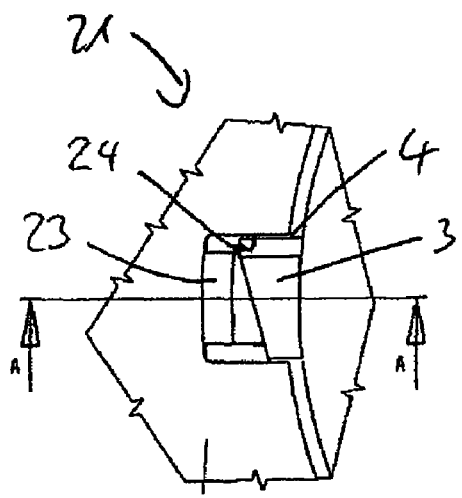
FIG. 8 shows a detail of FIG. 7.
Figure 7:
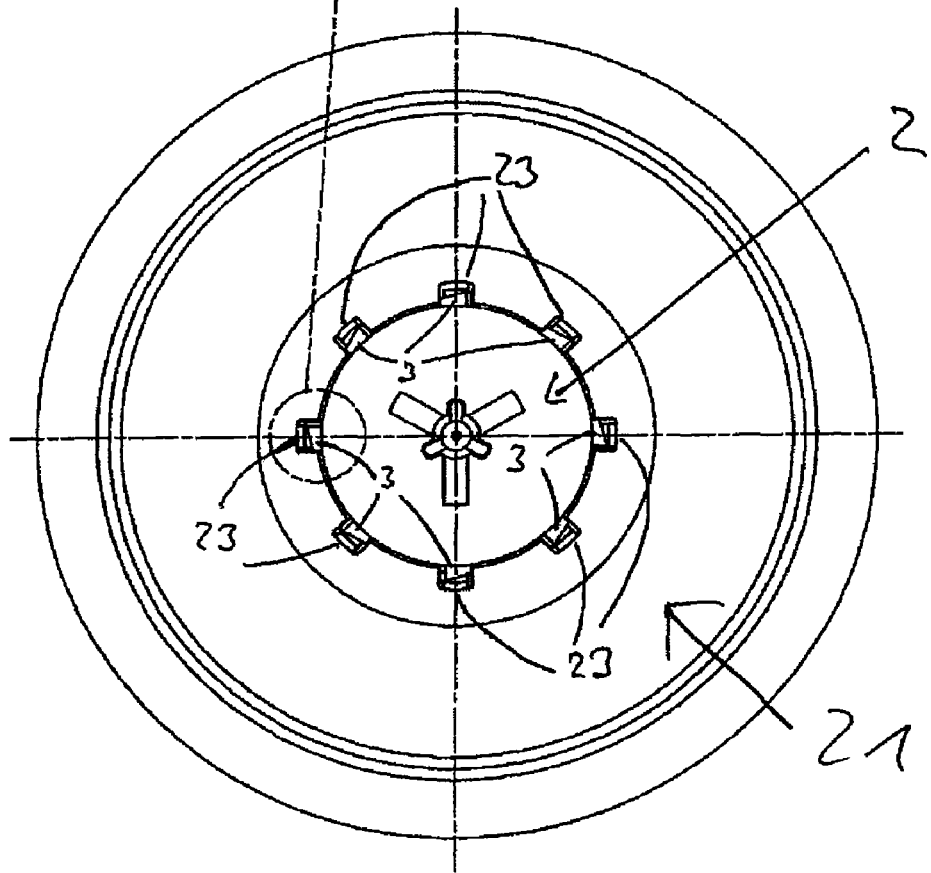
FIG. 7 shows a plan view of the pen needle according to FIG. 6 from the direction of the disposal container.

In FIG. 6, the pen needle according to aspects of the invention and the end of the injection pen 11 on which the pen needle is arranged are shown in a plan view, and, for better illustration of the release mechanism, the disposal container 20 is shown in a sectional view. The pen needle is already inserted with its main body 2 in the corresponding opening of the release mechanism 21 of the disposal container 20 and is held in this position by the latching means 3 of the needle holder and mating latching means 23 of the release mechanism 21. The mating latching means 23 have abutments 24, which engage behind abutments 4 of the latching means 3. In this position, the pen needle can no longer be easily pulled out from the opening of the release mechanism 21. The mating latching means 23 with their abutments 24 are designed to be flexible in the direction of the interior of the disposal container 20, in order to allow the pen needle to be pushed into the opening. Moreover, these mating latching means 23 with their abutments 24 can be designed to extend fully or only partially around the opening of the release mechanism 21, such that the abutments 4 of the latching means 3 are fully engaged from behind. During the insertion, the mating latching means 23 yield in the direction of pushing, and the latching means 3 slide along the mating latching means 23. After the latching means 3 have passed the mating latching means 23, these return to their starting position, and the abutments 24 of the mating latching means 23 engage behind the abutments 4 of the latching means 3. In this way, it is then no longer possible to easily pull the pen needle out from the opening of the release mechanism 21. This pushing in is therefore an irreversible procedure.

Figure 9:
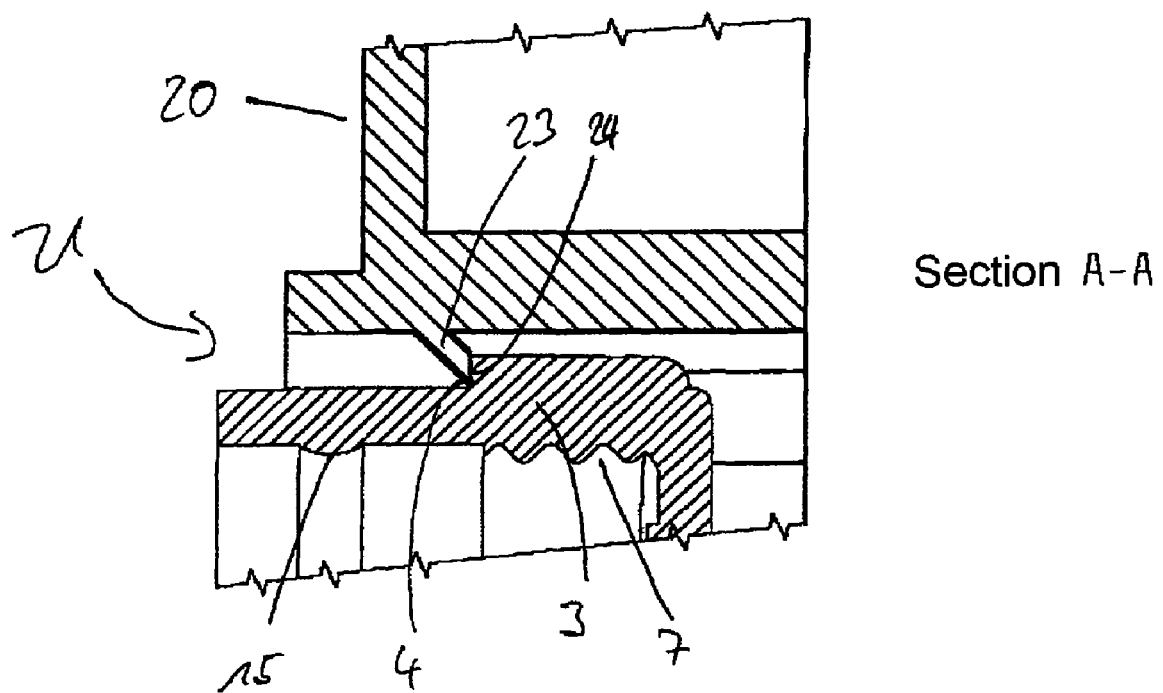
FIG. 9 shows a cross-sectional view of FIG. 8 along the section line A-A, without the injection pen.

If, in the pen needle according to aspects of the invention, the fit and secure hold on the injection pen 11 is effected not by threads but instead only by some other connecting means that engage in corresponding connecting means of the injection pen 11, the pen needle can be released from the injection pen by simply pulling the injection pen 11 out from the opening of the release mechanism 21. Such connecting means can, for example, be the undercuts 9 shown in the illustrative embodiment in FIGS. 1 to 4. However, as is shown in FIG. 9, a bead 15 can also serve as the connecting means. In this case, connecting means in the form of a trough are formed on the injection pen 11. As soon as the pen needle has been released from the injection pen 11, it drops into the disposal container 20 and is safely stored in the latter, being unable to be accidentally lost therefrom.

Alternatively or in addition, however, the pen needle can also engage with an outer thread of the injection pen 11 by means of an inner thread 7. Since the pen needle in this case has to be twisted off from the injection pen 11, recesses 26 are arranged inside the opening of the release mechanism 21, about the circumference thereof, as is shown in particular in FIGS. 7 and 8. Since, during insertion of the pen needle, the latching means 3 do not immediately come into engagement with the recesses 26, the latching means 3 are beveled along their longitudinal extent. The bevels thus formed permit simpler positioning of the latching means 3 in the recesses 26. After the latching means 3 are latched in the recesses 26, the pen needle can easily be twisted off from the injection pen 11. In the event that further connecting means are also used for the secure fit of the pen needle on the injection pen 11, these are disengaged from the injection pen 11 during the twisting-off of the pen needle. In this embodiment too, as soon as the pen needle is released from the injection pen 11, it falls unimpeded into the disposal container 12, where it is stored safely and permanently.

Figure 10:
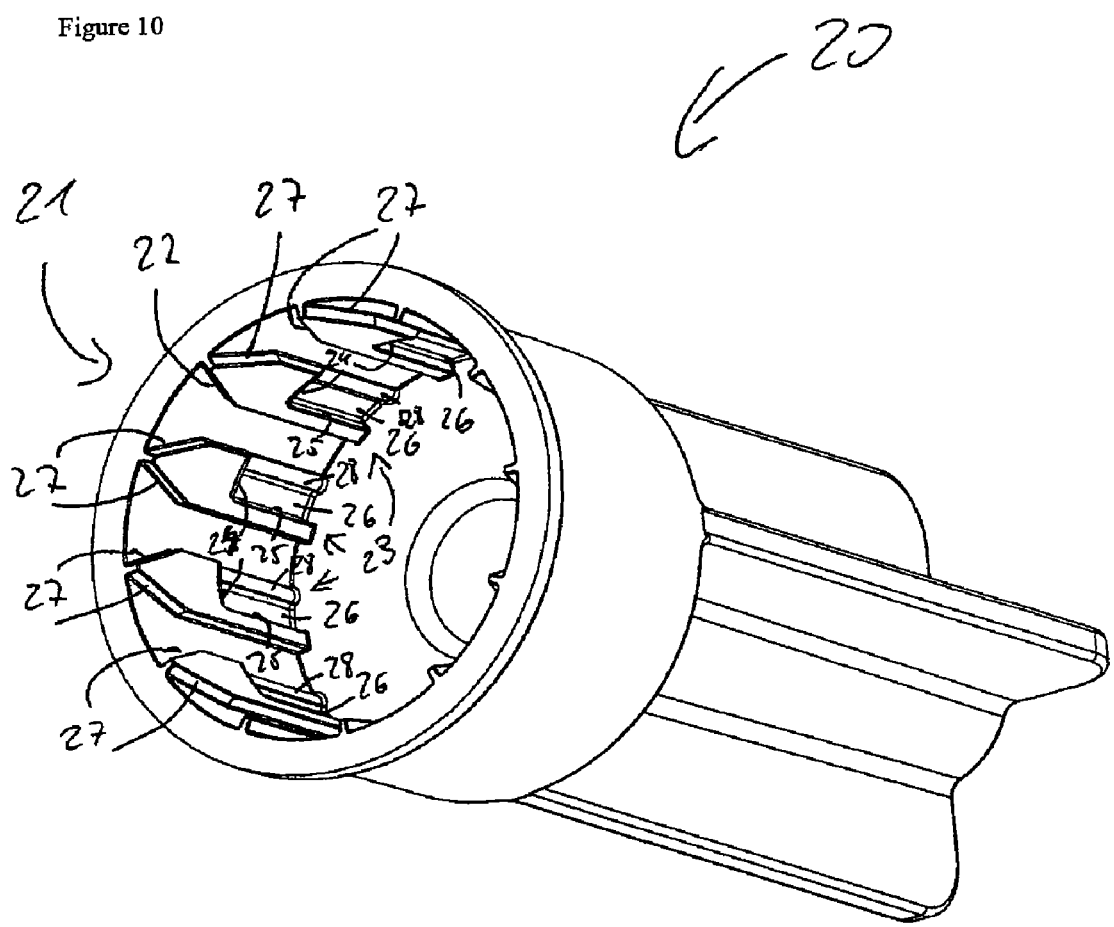
FIG. 10 shows a plan view of a storage container designed as a protective cap.

FIG. 10 is a plan view of a storage container 20 designed as a protective cap for a pen needle. This storage container 20 likewise comprises a release mechanism 21, as is shown in FIGS. 6 to 9. However, the latching means 23 of this release mechanism 21 comprise bevels 27, which facilitate insertion of the pen needle into the opening of the release mechanism 21. To release the pen needle, the latter is inserted into the opening of the release mechanism 21. In doing this, the latching means 3 designed as webs on the pen needle slide down along bevels 27 of the release mechanism 21 until the pen needle is completely received by the release mechanism. In order now to finally release the pen needle from the injection pen 11, the pen needle is turned until the latching means 3 designed as webs have moved across beads 28, such that they are fixed in the recesses 26 by the abutments 25. After the latching means 3 are fixed in the recesses 26, the beads 28 later prevent the latching means from accidentally sliding out of the storage position. If the pen needle is connected to the injection pen 11 by means of a thread, the pen needle is twisted further. By means of the abutments 25, the threads of the pen needle and of the injection pen disengage, such that the injection pen 11 can then be pulled out. By means of the abutments 24 of the mating latching means 23 of the release mechanism 21 of the protective cap designed as storage container 20, the pen needle is held back in the protective cap, such that it is safely stored in the latter.

LIST OF REFERENCE SIGNS

1—needle
2—main body
3—latching means
4—abutment
5—abutment
7—inner thread
8—reinforcing element
9—undercut
10—central longitudinal axis
11—injection pen
15—bead
17—depression
19—closure element
20—storage or disposal container
21—release mechanism
23—mating latching means
24—abutment
25—abutment
26—recess
27—bevel
28—bead

The invention claimed is:

1. A device for holding a needle and for releasable arrangement on an injection pen, said device having a main body, and the needle being arranged in the main body in such a way as to be substantially non-displaceable along a central axis of the main body, wherein latching means arranged on the circumferential surface of the main body are configured to be engaged by mating latching means of a release mechanism of a storage or disposal container for the device, wherein the latching means of the main body define a ramp for elastically deflecting the mating latching means of the release mechanism upon engaging the latching means of the main body with the mating latching means of the release mechanism, wherein the latching means of the main body also define a rear abutment, which intersects the ramp, upon which the mating latching means bear to limit translation of the main body in a single direction with respect to the container;

wherein the latching means further comprises a lateral abutment that intersects the ramp and the rear abutment, and the lateral abutment is configured to limit rotation of the main body with respect to the mating latching means of the container when the latching means of the main body are engaged with the mating latching means of the container.

2. The device as claimed in claim 1, wherein the latching means are webs.

3. The device as claimed in claim 1, wherein the rear abutments are configured to be engaged from behind by rear abutments of the release mechanism of a storage or disposal container for the device.

4. The device as claimed in claim 1, wherein the lateral abutments are configured to be engaged by lateral abutments of the mating latching elements of the release mechanism of a storage or disposal container for the device.

5. The device as claimed in claim 1, wherein the latching means are configured to be fixed in recesses formed by the mating latching means in the release mechanism of a storage or disposal container for the device.

6. The device as claimed in claim 1, wherein the latching means are distributed uniformly about the circumference of the main body.

7. The device as claimed in claim 1, wherein the latching means extend substantially from a proximal end of the main body to about a center of the main body.

8. The device as claimed in claim 1, wherein the latching means are arranged substantially in a central area of the main body.

9. The device as claimed in claim 1, wherein the main body has a hollow cylindrical design.

10. The device as claimed in claim 9, wherein the hollow cylindrical main body includes coupling means that are configured to engage with mating coupling means of an injection pen in order to permit releasable arrangement thereon.

11. The device as claimed in claim 10, wherein the coupling means comprise an inner thread in a hollow cylindrical region of the main body and the inner thread is configured to engage with an outer thread of a needle seat of an injection pen.

12. The device as claimed in claim 10, wherein the coupling means comprise at least one connecting means disposed in a hollow cylindrical portion of the main body and the at least one connecting means engage with at least one connecting means of a needle seat of an injection pen.

13. The device as claimed in claim 12, wherein the connecting means of the main body comprise at least one clip element that is configured to engage with at least one connecting means, comprising a mating clip element, on a needle seat of an injection pen.

14. The device as claimed in claim 1, wherein a reinforcing element is provided, in which the needle is held.

15. The device as claimed in claim 1 in combination with a storage or disposal container with a release mechanism for receiving the device.

16. The device as claimed in claim 15, wherein the release mechanism includes mating latching means that engage with the latching means that are arranged on a circumferential surface of the main body of the device.

17. The device as claimed in claim 16, wherein the mating latching means include rear abutments that are configured to engage behind rear abutments of the latching means of the main body of the device.

18. The device as claimed in claim 15 further comprising recesses provided in the release mechanism to fix the latching means of the main body of the device.

* * * * *